United States Patent [19]
Ricard et al.

[11] 4,207,441
[45] Jun. 10, 1980

[54] AUDITORY PROSTHESIS EQUIPMENT

[75] Inventors: Claude F. F. Ricard, Aix en Provence; Claude-Henri Chouard, Paris; Patrick MacLeod, Chatenay-Malabry, all of France

[73] Assignee: Bertin & Cie, Plaisir, France

[21] Appl. No.: 885,992

[22] Filed: Mar. 13, 1978

[30] Foreign Application Priority Data

Mar. 16, 1977 [FR] France ................................ 77 07824

[51] Int. Cl.$^2$ ............................................ H04R 25/00
[52] U.S. Cl. ........................................ 179/107 R; 3/1
[58] Field of Search ........................... 3/1, 1.1; 128/1; 179/107 E, 107 R, 107 FD; 325/28

[56] References Cited

U.S. PATENT DOCUMENTS

| | | | |
|---|---|---|---|
| 3,449,768 | 6/1969 | Doyle | 3/1 |
| 3,752,939 | 8/1973 | Bartz | 3/1 X |
| 4,025,721 | 5/1977 | Graupe et al. | 179/107 FD X |
| 4,063,048 | 12/1977 | Kissiah | 179/107 R |

OTHER PUBLICATIONS

*IEEE Journal of Solid State Circuits*, vol. SC-10, No. 6, Dec., 1975, New York, Gheewala et al., pp. 472-479.

Primary Examiner—Paul T. Sewell
Attorney, Agent, or Firm—Laurence R. Brown

[57] ABSTRACT

An equipment is described using n electrode sets implanted in the cochlea at n different locations for allowing the brain to identify n different frequencies. A receiver implant is coupled to the electrode sets through a selector and an external emitter is coupled to a single receiver coil of the implant by means of a single emitter coil. In the emitter the sound information signal is processed for forming n analysis signals of which the frequencies correspond to said n different frequencies and raster signals which are transmitted by modulating a high frequency a.c. signal. Each raster signal comprises at least n pulses of which the durations correspond to the energies to be transmitted to the n electrodes.

13 Claims, 3 Drawing Figures

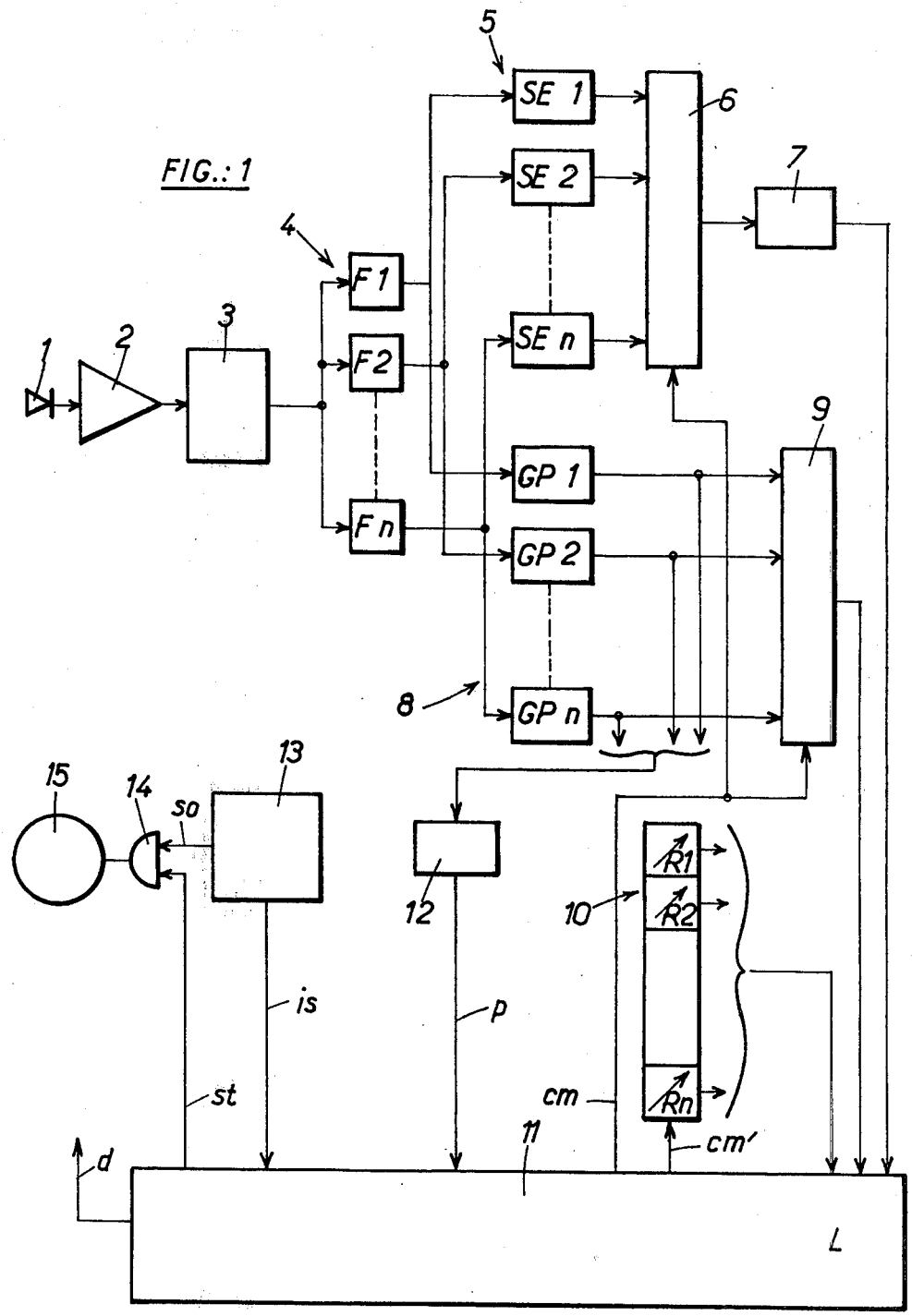

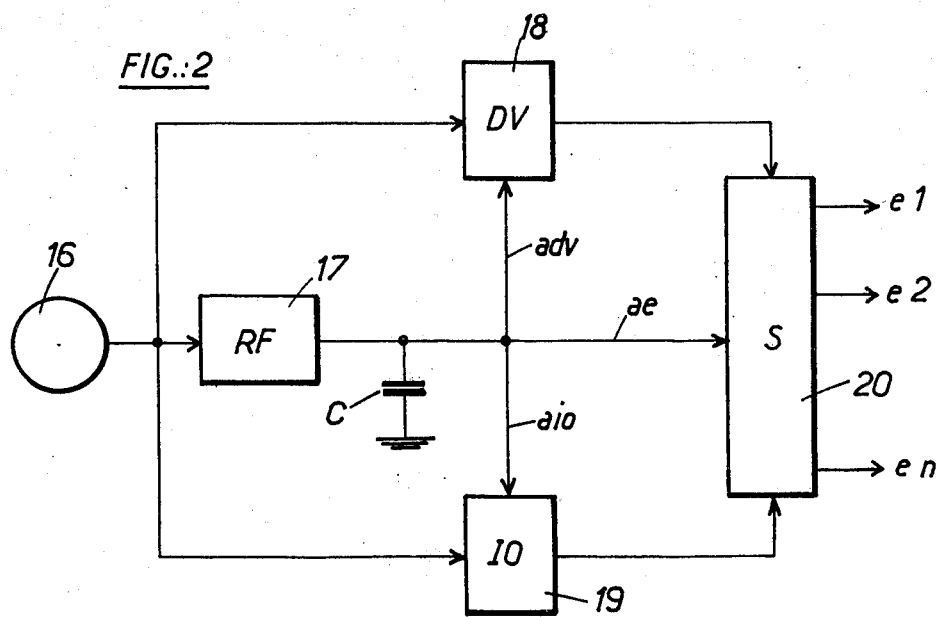
FIG.:2
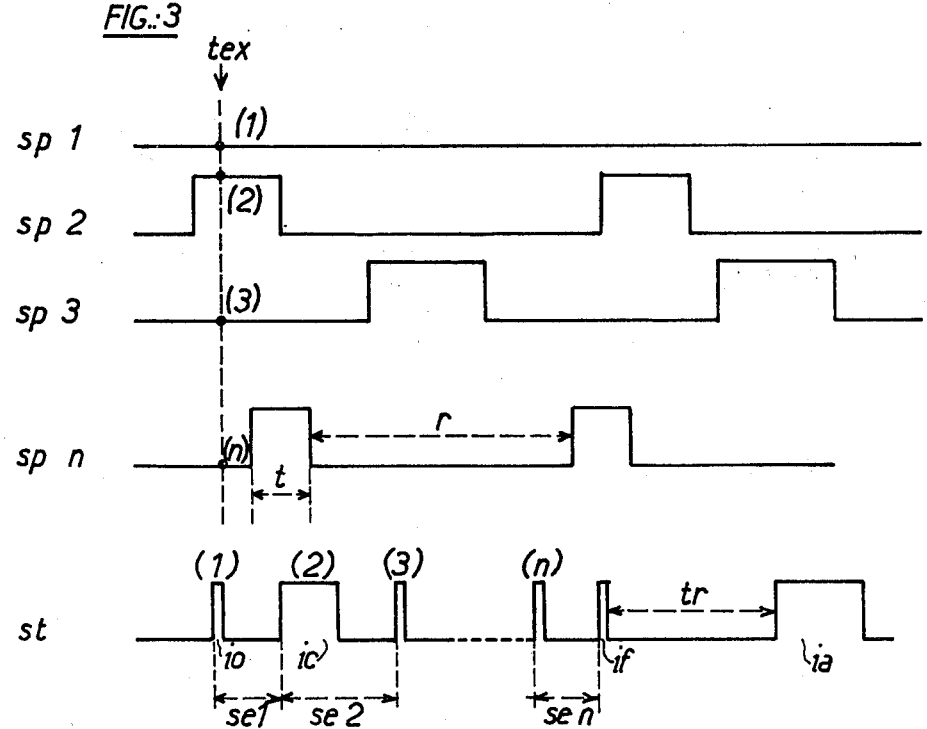
FIG.:3

AUDITORY PROSTHESIS EQUIPMENT

The invention relates generally to auditory prosthesis equipments and, in particular, it is related to such equipments which are intended for totally deaf patients and makes use of electrodes implanted in the cochleate nerve.

It is known that the sounds are mechanical vibrations which are transmitted to the liquids of the inner ear by the action of the ear-drum and the ossicles and which stimulate the hair cells of the cochlea. The hair cells transform the mechanical vibrations into electrophysiological signals and transmit said signals to the dendrites of the cochleate nerve fibers.

In the case of totally deaf patients, the hair cells are defective and the standard prosthesis apparatus are not efficient for they only more or less increase the mechanical energy supplied to the ear.

In a paper of the review "PRESSE MEDICALE" (35 1417, 1957), Doctors EYRIES and DJOURNO have stated that it is possible to stimulate directly the cochleate nerve under effect of an electrical current and to create a sensation of sound that, at this stage, is however indistinct and incomprehensible for the brain.

Auditory prosthesis apparatus have been now developed in which the defective outer and middle ears are practically short-circuited by a direct stimulation of the cochleate nerve. In said apparatus, the sound information is converted into electrical signals and transmitted to electrodes implanted in the cochlea through a plurality of wires. Said apparatus have a number of disadvantages; in particular, the wires transmitting the electrical signals to the electrodes must be introduced across the skin by means of a connector made of Teflon, causing discomfort to the patient.

Auditory prosthesis apparatus has also been developed in which the electrical pulses that stimulate the cochleate nerve are supplied by a receiver implanted under the skin and inductively coupled to an external emitter. Such a type of apparatus is described in the U.S. Pat. No. 3,449,768.

In the apparatus described in the above patent, a system is provided with n electrodes implanted in the cochlea. Each electrode is so positioned that it is assigned to one of n adjacent groups of fibers in the cochleate nerve. The n electrodes are coupled electromagnetically, and individually, through the skin, to the n outputs of a transmitter that is essentially provided with a microphone, an amplifier and n gates; the gates receive gating signals in sequence for the transmission of a signal representative of the sound information. Such an arrangement conduces to the stimulation by groups of the nerve fibers, and, in a group, the number of the stimulated fibers is the greater as the amplitude of the sound signal is high, the frequency of said signal being expressed by the brain from the recurrence frequency of the stimulation of a same number of fibers in the groups. It will be noted that the above described apparatus must be provided with n electromagnetical coupling devices, that is n transmitting coils coupled, through the skin, to the n receiving implanted coils. Such a conception is theoretically good, but it is difficult to follow in practice: it is not easy to find an arrangement with small sizes, without cross-talk between the n channels, and which does not require a very critical adjustment for the surgeon.

Now, it appears that each part of the cochlea in the direction of its length is selectively stimulated by a particular sound frequency and gives the sound sensation corresponding to said frequency to the brain. Thus it may be considered that it is possible to restore a certain level of differentiation of the sounds, the words and the music by stimulating separate parts of the cochlea while using signals which are themselves separated with respect to the main frequency bands of the received sounds. The signals are physiologically adapted and then they may be each transmitted through an electromagnetic channel for stimulating a particular electrode implanted in the cochlea. A ground electrode may be positioned in the proximity of the stimulated electrode; but it is known from a paper of the review "LA RECHERCHE" (vol. 6, No. 56, May 1975) that it is not necessary to have a ground electrode implanted in the cochlea if dielectric walls are implanted in the cochlea for dividing it into insulated compartments, that allows stimulating limited quota of the auditory nerve by parts and selectively.

It is the primary object of the present invention to allow totally deaf patients to recover a conversational capacity by giving them the capacity for understanding the words.

It is another object of the present invention to provide an improved apparatus in which only a small-sized and highly reliable electronic device is implanted in the body of the patient, without discomfort for said patient nor surgical complications.

It is a further object of the present invention to provide an equipment for an auditory prosthesis comprising a number of electrodes implanted in the cochlea, a receiving implant and an external emitter inductively coupled to the receiving implant through the skin.

The equipment according to the invention comprises n electrode sets implanted in the cochlea at the level of n discrete locations, which locations are chosen for allowing the brain to identify n discrete frequencies in the sound range; the emitter comprises essentially means for analysing sequentially at a frequency $F > 1/t$ n physiological pulse signals of which the minimum pulse duration is equal to t; the physiological signals are formed from n analysis signals derived from the information signal collected by the microphone for obtaining n frequencies corresponding to the n frequencies which may be identified by the brain, the emitter comprising an addition means for transmitting, through a single emitter coil and a single coil of the receiving implant, a high frequency signal of which the wave form is a raster signal with at least n pulses respectively assigned to the n electrodes and each representative of the energy to be transmitted to the electrode to which it is assigned; means are also provided in order that the receiving implant may be self-operated by the received signals.

Further objects, features and advantages of the invention will be better understood from the following description taken in connection with the accompanying drawings, in which:

FIG. 1 is a block diagram of the emitter,

FIG. 2 is a block diagram of the receiving implant,

FIG. 3 illustrates different graphs of signals in the emitter and in the receiver.

In the emitter circuits of the FIG. 1, the microphone 1 is coupled to an amplifier 2 of which the output is coupled to a compressor 3.

In the compressor 3, the dynamic characteristic of the sound information signal is adapted to the dynamic characteristic of the ear. For example, a noise varying from 40 dB (treshold of perception) to 100 dB (treshold of painful noise) is compressed in the circuit 3 for obtaining a difference equal to 4 dB and the compression is constantly proportional to the instantaneous noise which is collected so that the perception scale is not deformed in the brain (normally, such a compression is performed in the ear-drum and the middle ear). Conveniently, the compressor 3 is comprised of an analog peak level detector, a computer which calculates a control digital signal from the analog value supplied by the detector, and an analog/digital multiplier which transforms the analog signal supplied by the amplifier 2 into a signal of which the amplitude is modulated by the control digital signal (the compressor circuits are not shown in details).

The compressor 3 is connected to the input of an analysing network 4 which transforms the sound information signal, after it has been amplified and compressed, into n analysis signals of which the frequencies correspond to the n frequencies which may be identified by the brain. To this end, the network 4 comprises n filters; F1, F2, . . . Fn which are respectively synchronized to n frequencies corresponding to the n frequencies that the brain may identify with the aid of the n electrodes coupled to the receiver implant. For example, the network 4 may be comprised of at least eight filters (for eight implanted electrodes); said filters allows analysing a frequency band containing the information convenient for a proper understanding, for instance a 300 Hz–3000 Hz band; and, by a spectrum transposition, the identified frequencies may be comprised for instance in the 100 Hz–10 kHz band.

The output terminal of the network 4 is connected to two networks i.e. an amplitude calculating network 5 and a physiological signal forming network 8; that is to say each filter of the network 4 is connected to a corresponding energy follower SE in the network 5 and to a corresponding "modulator" GP of the network 8.

On the other hand, the output terminals of the circuits SE1, SE2, . . . SEn of the network 5 are connected to a multiplexer 6, the circuits GP1, GP2, . . . GPn having their output terminals connected to another multiplexer 9.

In the network 5, each energy follower SE calculates the analog mean value of the amplitudes of the signals it receives from the filter F, between two selections performed by the sequential analysing means that the multiplexer 6 also contains. The analog signals supplied by the multiplexer 6 are converted into digital signals in the digital/analog converter 7.

Each circuit GP of the network 8 is operated by the frequency analysis signal supplied by the filter F to which it is connected. In fact, each "modulator" GP is a generator generating a signal which is physiologically adapted (a number of said physiological signals are shown in FIG. 3). The physiological signals supplied by the circuit GP1, GP2, . . . GPn are pulse signals with pulses of which the minimum duration is equal to t and which alternate with rest times r which are relatively long times. The values of t and r have been determined with a sufficient accuracy from laboratory physiological researches. The pulse durations may be for instance comprised between 0.2 and 0.4 ms, the rest times ranging about 0.5 ms. The amplitude of the pulses of the physiological signal is constant and corresponds to a maximum value. It has been stated that each circuit GP is operated by the output signal of the filter F to which it is connected; in fact, during the sequential analysis, the multiplexer 9 states that there is or not a high level at the output of the circuit GP which has been selected, depending on the constitution of the sound information signal collected by the microphone and the form of the physiological signal.

The outputs of the analog/digital converter 7 and of the multiplexer 9 (which is a logic multiplexer) are connected to a logic circuit 11 (L) which, on the other hand, controls in synchronism the sequential analysis performed by the two multiplexers 6 and 9 (control wire cm). The logic circuit 11 controls simultaneously the selection of the adjustment blocks R1, R2, . . . Rn of the matching network 10 (control wire cm').

A specific preadjustment for every patient and each equipment is performed in the matching network 10. Indeed the efficiency of an electrode implanted in the cochlea of a patient depends on the number of living cells and on the way said electrode has been implanted; it is thus necessary to correct the data collected for a particular electrode. Consequently, the blocks R1, R2, . . . Rn are previously adjusted with the co-operation of the patient after the electrodes have been implanted. A block R which has been selected supplies a matching or correcting multiplying number which is transferred to the logic circuit 11 when the output signals of the corresponding circuits GP and SE are analysed.

In the logic circuit 11, the data supplied by the multiplexer 9, the analog/digital converter 7 and the matching network 10 are processed for obtaining a pulse signal at (or raster signal) such as the signal shown FIG. 3; the pulses of said signal are very short (pulse io for the analysis of sp1) when the level of the analysed physiological signal is low and said pulses are width-modulated (pulse ic for the analysis of sp2) when the level is high; the width of a pulse such as ic depends on the value of the digital signal which at that time is supplied by the analog/digital converter 7 and on the correcting number supplied by the matching network 10. That is to say the information of an impulse such as ic is amplitude corrected.

The pulse signal st is transmitted to the input of an AND gate 14; it forms the gating signal for allowing said gate to transfer the high frequency signal so generated by the oscillator 13. Preferably, the oscillation carrier frequency is ranging about 3 MHz. The gate 14 is connected to the emitter coil 15 (the coil 15 is shown in the shape of a ring-coil; such a shape is in fact adapted to the shape of the antenna constituted by said coil which is mounted on a side of spectacles worn by the patient and connected to a portable emitter box by means of a flexible wire; the exact position of the antenna is chosen in the course of post-operative tests and determined by the position of the receiver implant to which it transmits the energy and the necessary information for hearing).

It has been previously stated that $F > 1/t$. That means that one pulse of the physiological signal is analyzed a number of times. For example, if the minimum duration t is equal to 0.2 ms, the pulse of which the duration is equal to t will be scanned four times if the scanning frequency is equal to 20 kHz. Such a value is chosen in dependence on the accommodating time of the ear. A circuit 12 is also illustrated FIG. 1, which circuit is a low consumption surveillance circuit; it operates for limiting the energy consumption. To this end, the circuit 12 is connected to the outputs of the circuits GP1, GP2, . . . GPn and, as it detects a signal appearing at the output of said circuits, it controls the emitter circuits only at this time. That is to say the emitter circuits are normally disconnected from their power supply circuits and are put into service only when the logic circuit supplies a gating signal d is a signal of presence p is supplied by the surveillance circuit 12 (there are indeed many silence times in the course of a conversation and the noise level frequently falls under the sensitivity treshold of the microphone-filter assembly; further, due to the characteristics of the word and of the physiological signal, the pulse density to transmit is quite lower than 100%).

At various times, the graphs illustrated FIG. 3 are above-mentioned. The graphs sp1, sp2, sp3, spn are examples of signals which can appear at the output of the circuits GP1, GP2, GP3, GPn. In said example, only the channel with the filter F1 and the circuit GP1 is not operated. At the time tex of a scanning procedure, the sequential analysis will conduce, at the output of the logic circuit, to the formation of pulses in series which form the raster signal st, since:

sp1 is at a low level (1), conducing to the formation of a pulse io of short duration, sp2 is at a high level (2), conducing to the formation of a long pulse ic of which the duration depends on the multiplying numbers supplied by the converter 7 and the network 10, sp3 and spn are at a low level (3 and n), conducing to the formation of two pulses of the type io.

For example, the pulses io have a duration ranging about one microsecond, the pulses ic having a duration of 10 microseconds for instance.

The raster signal st is illustrated FIG. 3 with two additional pulses; the pulse if is a transmission end pulse (i.e. a pulse formed at the end of the analysis sequence); as it will be described later, the pulse if is used in the receiver implant and it is used in the emitter for resetting the logic circuit which will be then waiting for a presence signal p (supplied by the surveillance circuit) and for resetting the other circuits of the emitter; the pulse ia has a relatively long duration and is in fact a pulse indicating the beginning of an analysis sequence; the pulse ia is thus a pulse pertaining to the sequence which follows the one which is illustrated in the graph. The pulses if and ia are formed by the logic circuit of which the clock circuit may be otherwise constituted by the oscillator 13 as it is stated by the wire is illustrated FIG. 1. The function of the pulse ia will be explained later; the time tr separating the pulse ia from the pulse if generated during the preceding analysis is of long duration for a number of reasons which will be also explained later.

The diagram of the receiver implant is illustrated FIG. 2 in a simplified manner, the major parts of the circuits being in the emitter. The receiver implant comprises an input coil 16, a selector 20 (S) of which the output terminals e1, e2, . . . en are respectively coupled to the n electrodes, a channel demodulator 18 (DV), a reset integrator 19 (IO), and a rectifier-filter 17 (RF) with an output storage capacitor C.

It has been previously stated that the arrangement is such that the receiver implant is self-operated, i.e. it is fed from the signals it receives. It has been also stated that the transmitted signal is a high frequency signal of which the waveform is defined by the raster signal st. The high frequency signal is rectified and filtered, then the resultant d.c. signal is stored in the capacitor and used for feeding the receiver implant. Because it is necessary to store some signal in the capacitor before the raster signal is demodulated, said raster signal is preceded by the pulse ia which is illustrated FIG. 3 in the graph st. But it is obvious that all the pulses of the raster signal are used for charging the capacitor C.

The circuit 18 is a channel demodulator. In other words, said circuit controls the sequential selection of the electrodes implanted in the cochlea by controlling the stepping of the selector S. The stepping is controlled by the front edge of the raster pulses; the graph st of the FIG. 3 illustrates the time se1 which is the time at which is selected the electrode connected to the output terminal e1 of the selector 20, and the time se2 which is the time at which is selected the electrode connected to the output terminal e2 of said selector. The demodulator 18 is fed by means of the wire adv.

When an electrode is selected, it is fed from the storage capacitor C by means of the wire ae. The energy transmitted to said electrode thus depends on the duration of the raster pulse comprised in its selecting time duration. It would be noted that all the electrodes are selected in sequence and that all the electrodes are therefore fed with current whatever be the result of the sequential analysis performed in the emitter. But, in fact, the same se1 for instance which contains the pulse io formed for a low level is such that the energy transferred to the electrode does not reach the perception treshold of the auditory nerve.

The selector 20 (S) has a dummy channel and the time tf following the pulse if at the end of the selection time sen of the $n^{th}$ electrode is detected by the reset integrator 19 (IO) and, under control of said integrator, the selector is put on its dummy channel. The reset integrator 19 is fed by means of the wire aio.

The invention is not limited to the embodiment described above, and all changes and modifications not constituting departures from the spirit and scope of said invention are intended to be covered by the following claims.

We claim:
1. An equipment for an auditory prosthesis comprising in combination:
a system with n sets of electrodes implantable in the cochlea at n different locations so chosen that when they are stimulated the electrodes allow the brain to identify n different frequencies comprised in the audible range;
an external emitter with means for sequentially analysing n physiological pulse signals having a minimum pulse duration equal to t; means for analysing the sound information signal collected by a microphone and thus forming n analysis signals of which the frequencies correspond to the n frequencies which can be identified by the brain, means for processing the analysis signals and thus forming the physiological pulse signals, and means for transmitting through the skin and by means of a single emitter coil a high frequency signal having a waveform defined by raster signals including said sequential physiological pulse signals, each raster signal having at least n sequential pulses respectively assigned to the n electrode sets and each having a pulse duration t representative of the energy to be transmitted to the electrode set to which it is assigned;
a receiver implant with a single receiver coil inductively coupled with the emitter coil and provided with means for allowing said receiver implant to be self-operated by the received signals.

2. An equipment as claimed in claim 1, in which the means for processing the analysis signals are comprised of means for calculating the mean energy of each analysis signal between two successive scanning procedures performed by the sequential analysis means, and multiplying means for forming, in a raster signal and for the electrode set of which the location in the cochlea allows identifying the frequency fi, a pulse of which the duration is proportional to the mean energy calculated for the analysis signal having the frequency fi.

3. An equipment as claimed in claim 1, in which the means for allowing the receiver implant to be self-operated by the received signals are comprised of a rectifier-filter coupled to the single input receiver coil and of a storage capacitor coupled to the rectifier-filter, said rectifier-filter and said storage capacitor forming the power-supply circuit of the other circuits of the receiver implant, said power-supply circuit being fed by the high frequency signal of which the waveform is defined by raster signals.

4. An equipment as claimed in claim 3, in which the emitter further includes means for forming in each raster signal a transmission start pulse of which the duration is such that, as the high frequency a.c. signal said pulse contains is rectified and filtered, the charge of the storage capacitor is sufficient for the initial feeding of the other circuits of the receiver implant.

5. An equipment as claimed in claim 3, in which the receiver implant comprises essentially a selector for sequentially connecting the n electrode sets and a channel demodulator which controls the stepping of the selector and thus the stimulation of the n electrode sets in dependence on the mean energy information contained in each of the n pulses of the raster signal.

6. An equipment as claimed in claim 5, in which the selector of the receiver implant comprises a closing circuit for connecting the power-supply circuit to the $i^{th}$ electrode set under control of the demodulator channel, the connection being established for the duration of the $i^{th}$ among the n electrodes pulse of the raster signal.

7. An equipment as claimed in claim 2, including in said external emitter a logic circuit in which the sequential analysing means of the emitter comprises essentially a first multiplexer controlled by the logic circuit, the means for analysing the sound information signal being comprised of n filters synchronized to n frequencies comprised in a range containing the information necessary for the understanding and corresponding to the n frequencies which can be identified by the brain, and the means for processing the analysis signals being comprised of n formers of physiological signals respectively connected to the output terminals of the n filters, the first multiplexer connecting the output terminals of the n formers to the logic circuit in sequence.

8. An equipment as claimed in claim 7, in which the emitter comprises a compressor coupled to the output terminal of the microphone and the input terminals of the n filters, said compressor being provided for adapting the dynamic characteristic of the sound information signal to the dynamic characteristic of the ear.

9. An equipment as claimed in claim 7, in which the means for calculating the mean energy of the n analysis signals comprises essentially a network with n integrators-energy followers respectively connected to the output terminals of the n filters, and a second multiplexer controlled by the logic circuit in synchronism with the first multiplexer, an analog/digital converter connected to an input terminal of the logic circuit and which is connected in sequence to the output terminals of the n energy followers under control of said second multiplexer, the analog/digital converter being provided for supplying in sequence n first multiplying numbers corresponding to the n calculated mean energies, and the multiplying means forming a part of the logic circuit for modifying the duration of n pulses characterizing the sequential scanning of the n formers in function of the values of the n first multiplying numbers.

10. An equipment as claimed in claim 9, in which the emitter further comprises a matching network with n pre-adjusting blocks, said blocks being selected in sequence and in synchronism with the first and the second multiplexers and thus connected to the multiplying means of the logic circuit for supplying them with n second multiplying numbers which depend respectively of the efficiency of the n electrode sets implanted in the cochlea, and the multiplying means being provided for modifying the duration of n pulses characterizing the sequential scanning of the n formers in function of the values of the n second multiplying numbers.

11. An equipment as claimed in claim 1, in which the transmission means comprises essentially a high frequency oscillator coupled to the single emitter coil and an AND-gate connected between said oscillator and said coil, the gating signals of said AND-gate being formed by the high level pulses of the raster signal.

12. An equipment as claimed in claim 11, in which the clock of the logic circuit is constituted by the high frequency oscillator.

13. An equipment as claimed in claim 10, in which the emitter further comprises a surveillance circuit of which the input terminal is connected to the output terminals of the n formers of physiological signals and of which the output terminal is connected to the logic circuit, said surveillance circuit being provided for supplying a presence pulse as soon as it detects a signal at the output of one of the formers, and the logic circuit being provided for supplying a start signal under control of a presence pulse in order to starting the emitter circuits for a duration corresponding to a single analysis sequence, said logic circuit being also provided for generating a transmission end signal which is transmitted to the receiver implant and used in said implant for starting an integrator provided for resetting the selector, and means being provided for establishing a relatively long dead time between the transmission end pulse of the $p^{th}$ raster signal and the transmission start pulse of the $(p+1)^{th}$ raster signal when the surveillance circuit detects continuously a signal at the output of one of the formers.

* * * * *